United States Patent [19]

Fournier et al.

[11] Patent Number: 4,714,700
[45] Date of Patent: Dec. 22, 1987

[54] N-SUBSTITUTED 2,4-DIALKOXY BENZENESULFONAMIDES AND PHARMACEUTICAL COMPOSITIONS

[75] Inventors: Jean-Paul Fournier, Versailles; Patrick Choay, Paris, both of France

[73] Assignee: Choay S.A., Paris Cedex, France

[21] Appl. No.: 700,478

[22] Filed: Feb. 12, 1985

Related U.S. Application Data

[62] Division of Ser. No. 370,168, Apr. 20, 1982, abandoned.

[51] Int. Cl.[4] ................ A61K 31/435; A61K 31/535; C07D 295/12
[52] U.S. Cl. .................................... 514/229; 514/255; 514/331; 514/427; 514/428; 514/604; 544/159; 544/398; 546/232; 548/561; 548/569; 564/89
[58] Field of Search ............... 514/229, 255, 331, 427, 514/428, 604; 544/159, 398; 546/232; 548/561, 569; 564/89

[56] References Cited

U.S. PATENT DOCUMENTS 4,132,786  1/1979  Moreau et al. ..................... 564/87

OTHER PUBLICATIONS

Fournier et al, *Chemical Abstracts*, vol. 98 (1983), No. 178939z.

*Primary Examiner*—Robert W. Ramsuer
*Attorney, Agent, or Firm*—Weiser & Stapler

[57] ABSTRACT

The invention relates to new N-substituted benzenesulfonamides, the process for their preparation and their use.

The compounds according to the invention correspond to the general formula (I):

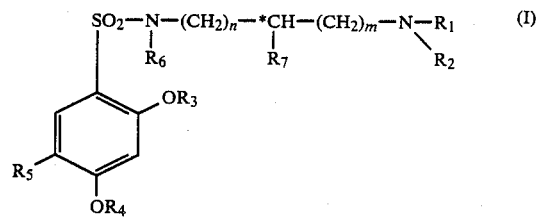

in which:
n and m have values from 0 to 4;
$R_3$ and $R_4$ represent in particular a lower alkyl radical;
$R_1$ and $R_2$ represent in particular hydrogen atoms, linear or branched alkyl groups having from 1 to 4 carbon atoms;
$R_5$ represents particularly a hydrogen atom, a halogen, the $NO_2$, $NH_2$, or $CF_3$ group;
$R_6$ and $R_7$ represent in particular a hydrogen atom, an alkyl radical of 1 to 6 carbon atoms.

The invention is useful in the preparation of tranquilizing or anxiolytic medicines.

10 Claims, No Drawings

N-SUBSTITUTED 2,4-DIALKOXY BENZENESULFONAMIDES AND PHARMACEUTICAL COMPOSITIONS

This application is a division of application Ser. No. 370,168, filed Apr. 20, 1982.

The invention relates to new compounds of the N-substituted benzenesulfonamide type as well as to their corresponding salts. The invention also relates to a process for preparing these compounds. The invention finally relates to new medicaments containing, as active principle, these new compounds of the N-substituted benzenesulfonamide type as well as their salts obtained with physiologically acceptable organic or inorganic acids. The new N-substituted benzenesulfonamides according to the invention correspond to the general formula:

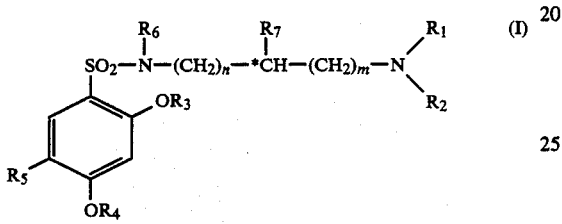
(I)

in which:
n and m independently from each other take values from 0 to 4;
$R_3$ and $R_4$ each represent, independently from each other, a lower alkyl radical having from 1 to 4 carbon atoms;
$R_1$ and $R_2$ represent, independently from each other, hydrogen atoms, linear or branched alkyl groups having from 1 to 4 carbon atoms, or forming conjointly with the nitrogen atom a heterocyclic nitrogenous group with 5 or 6 links, particularly a pyrrolidino, morpholino, piperazinyl, pyrrole or piperidino group substituted or not by linear or branched alkyl radicals having from 1 to 4 carbon atoms;
$R_5$ represents a hydrogen atom, a halogen, the $NO_2$, $NH_2$, $CF_3$ group or an alkoxy radical having from 1 to 4 carbon atoms, or an alkylsulfonyl radical having from 1 to 4 carbon atoms;
$R_6$ and $R_7$ representing, independently from each other, a hydrogen atom, an alkyl radical with 1 to 6 carbon atoms or a cycloalkyl radical with 3 to 6 carbon atoms.

The invention also relates to the addition salts of compounds of formula (I) obtained with physiologically accpetable organic or inorganic acids.

The invention is also concerned, when $R_7$ is different from the hydrogen atom, with all the optical isomers of the compounds of formula (I) as well as their salts obtained with physiologically acceptable organic or inorganic acids.

As physiologically acceptable organic or inorganic salts, may be mentioned, for example, the hydrochloride, the hydrobromide, sulfates, phosphates, methane sulfonate, acetate, fumarate, succinate, lactate, pyruvate, citrate, tartrate, maleate, malonate, benzoate, salicylate, 2,6-dichloro-benzoate, trimethoxy benzoate, diamino benzene sulfonate, chromoglycate, benzene sulfonate, dipropyl acetate and 1-glucose phosphate.

In the rest of the description, the compounds of formula (I) according to the invention in which $R_5$ represents a hydrogen atom, are denoted by disubstituted compounds and whose in which $R_5$ has the aboveindicated meaning, with the exception of hydrogen, are denoted by trisubstituted compounds.

A preferred class of compounds according to the invention is constituted by the 2,4-dialkoxy benzenesulfonamides possibly substituted in the 5 position and corresponding to the following formula (II):

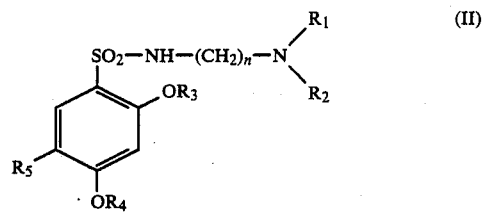
(II)

in which:
n takes the values of 1 to 4, particularly 2 or 3;
$R_3$ and $R_4$ each represent, independently from each other, a lower alkyl radical having from 1 to 4 carbon atoms,
$R_1$ and $R_2$ represent independently from each other, hydrogen atoms, linear or branched alkyl groups having from 1 to 4 carbon atoms, or forming conjointly with the nitrogen atom a nitrogeneous heterocyclic group with 5 or 6 links, particularly a pyrrolidino, morpholino, piperazinyl, pyrrole or piperidino group substituted or not by linear or branched radicals having from 1 to 4 carbon atoms,
$R_5$ represents a hydrogen atom, halogen, the group $NO_2$, $NH_2$, $CF_3$, an alkoxy radical having from 1 to 4 carbon atoms, or an alkyl sulfonyl radical having from 1 to 4 carbon atoms.

A preferred class of compounds according to the invention is constituted by the 2,4-dimethoxy benzenesulfonamides substituted in the 5 position and corresponding to the following general formula (III):

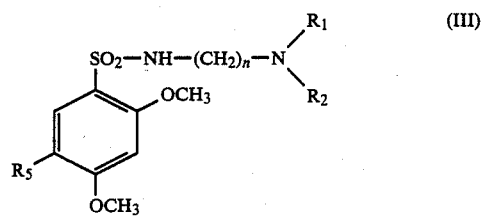
(III)

in which n, $R_1$, $R_2$, $R_5$ have the aboveindicated meanings.

An advantageous class of compounds according to the invention is constituted by the 2,4-dimethoxy benzenesulfonamides of formula (III) in which n, $R_1$, $R_2$ have the aboveindicated meanings and $R_5$ represents hydrogen. These compounds are disubstituted.

Among the disubstituted compounds an advantageous class of compounds according to the invention is constituted by the compounds of formula (III) in which:
n is 2 or 3;
$R_5$ represents a hydrogen atom;

represents one of the radicals selected from the group comprising dimethylamino, diethylamino, pyrrolidino, piperidino, morpholino or piperidino radicals substituted by a methyl group at the 2 position.

An advantageous class of compounds according to the invention is constituted by the 2,4-dimethoxy benzenesulfonamides substituted at the 5 position, of formula (III) in which n, $R_1$ and $R_2$ have the aboveindicated meanings, $R_5$ has also the aboveindicated meaning, with the exception of hydrogen. These compounds are trisubstituted.

Among these trisubstituted compounds, an advantageous class of compounds according to the invention is constituted by the compounds of formula (III), in which $R_5$ represents Cl, Br, $OCH_3$, $SO_2C_2H_5$, $SO_2nC_3H_7$, $SO_2iC_3H_7$.

Another advantageous class of trisubstituted compounds according to the invention is constituted by the compounds of formula (III) in which $R_5$ represents Cl, Br, $OCH_3$.

Another class of preferred trisubstituted compounds according to the invention is constituted by the compounds of formula (III) in which:
n is 2 or 3;
$R_5$ represents the $OCH_3$, Cl, Br, $SO_2-CH_3$, $SO_2C_2H_5$, $SO_2nC_3H_7$, $SO_2iC_3H_7$;

represents one of the radicals selected from the group comprising dimethylamino, diethylamino, pyrrolidino, piperidino, morpholino or piperidino radicals substituted by a methyl group particularly at the 2 position.

A preferred class of trisubstituted compounds according to the invention is constituted by the compounds of formula (III) in which:
n is 2 or 3;
$R_5$ represents Cl, Br, $SO_2CH_3$, $SO_2C_2H_5$; and

represents the pyrrolidino, piperidino or morpholino radical.

A particularly advantageous class of trisubstituted compounds is constituted by the compounds of formula (III) in which:
n is 2 or 3;
$R_5$ represents Cl, Br, $SO_2CH_3$; and

represents the pyrrolidino, piperidino or morpholino radical.

Another advantageous class of trisubstituted compounds according to the invention is constituted by the compounds of formula (III) in which:

n is 3;
$R_5$ represents Cl, Br, $SO_2CH_3$, $OCH_3$; and

represents the morpholino radical.

Another advantageous class of trisubstituted compounds according to the invention is constituted by the compounds of formula (III) in which:
n is 2;
$R_5$ represents $SO_2C_2H_5$; and

represents the diethylamino radical
or n is 3;
$R_5$ represents $SO_2C_2H_5$; and

represents the dimethylamino or diethylamino radical.

The compounds of these various preferred groups are advantageously in the form of salts, particularly the hydrochloride.

To form the compounds according to the invention, it is possible to have recourse to the sulfohalides, particularly to the sulfohalides of formula (IV):

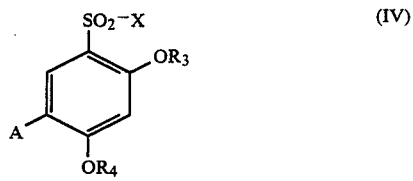

(IV)

in which X is a halogen group, particularly bromine or preferably chlorine, $R_3$ and $R_4$ each representing, independently from each other, a lower alkyl radical having from 1 to 4 carbon atoms, A has any one of the aboveindicated meanings for $R_5$, with the exception of $NH_2$ (that is to say represents hydrogen, a halogen, alkoxy radicals having from 1 to 4 carbon atoms, alkylsulfonyl groups having 1 to 4 carbon atoms, or the group $NO_2$, $CF_3$).

To prepare the sulfohalides of formula (IV) indicated above, particularly the sulfochlorides of formula (V):

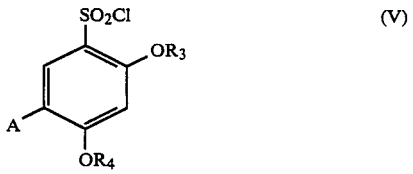

(V)

in which A, $R_3$ and $R_4$ have the aboveindicated meanings, recourse may be had to the arylamine of formula (VI):

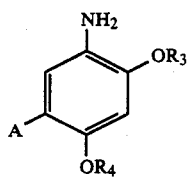 (VI)

in which A, R$_3$ and R$_4$ have the aboveindicated meanings, and from which:

(a) the diazonium salt is formed particularly the diazonium chloride of formula (VII). This diazonium salt is obtained particularly by reacting the arylamine in a solution of the corresponding halo acid, particularly hydrochloric acid, with a solution of a nitrite of alkali metal, and keeping the reaction mixture at a temperature preferably lower than about 10° C.

(b) the diazonium salt obtained is then reacted in solution with sulfurous anhydride. The operation is preferably carried out in the presence of acetic acid as well as of a catalyst suitable for assisting in the conversion of the diazonium group into a sulfohalide group, particularly sulfochloride. This catalyst is, for example, based on copper (modified Sandmeyer reaction).

The steps (a) and (b) of this reaction applied by way of example to the preparation of sulfochlorides of formula (V) may be represented as follows:

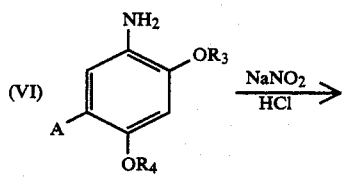

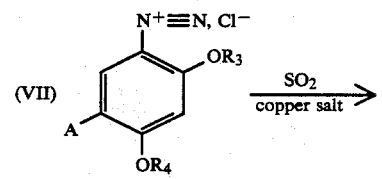

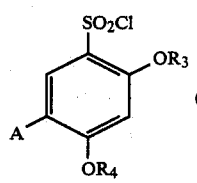 (V)

By way of preferred arylamines for the preparation of the sulfochlorides of formula (V) may be mentioned:
2,4-dimethoxy aniline
5-chloro 2,4-dimethoxy aniline,
5-bromo 2,4-dimethoxy aniline,
2,4,5-trimethoxy aniline,
2,4-dimethoxy 5-methylsulfonyl aniline,
2,4-dimethoxy 5-ethylsulfonyl aniline,
2,4-dimethoxy 5-propylsulfonyl aniline,
2,4-dimethoxy 5-isopropylsulfonyl aniline.

To prepare the sulfochlorides of formula (V) in which A has the aboveindicated meaning, it is also possible to proceed by sulfonation or halogenosulfonation, preferably chlorosulfonation of the compound of formula (VIII) in which A, R$_3$ and R$_4$ have the aboveindicated meanings:

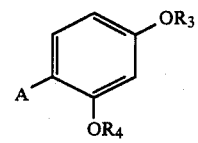 (VIII)

In the case of sulfonation (by reaction of the compound (VIII) with sulfuric acid) in a first step the sulfonic acid of formula (IX) was obtained:

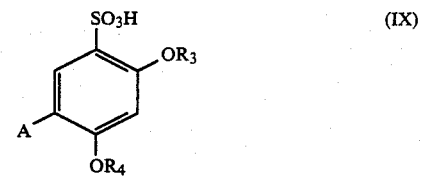 (IX)

The acid (IX) obtained can then be converted into a salt of an organic or inorganic base, by the action of the suitable base such as sodium hydroxide, potassium hydroxide or pyridine.

This salt is represented by the formula (X) below:

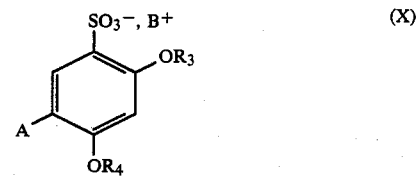 (X)

in which B$^+$ represents a metal, notably an alkali or alkaline-earth metal, and A has any one of the aboveindicated meanings. The chloride of formula (V) is then obtained by the action on the compound of formula (IX)—or on the corresponding organic or inorganic salt of formula (X)—of a chlorinating agent, such as thionyl chloride, phosphorus pentachloride, or phosphorus oxychloride.

By way of example, the reaction diagram for the production of compounds (V) in which A has any one of the aboveindicated meanings from compounds of formula (VIII) can be represented as follows:

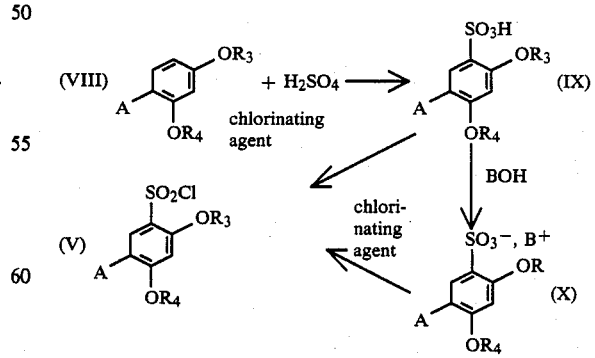

In the case of chlorosulfonation, the chlorosulfonic acid is reacted with the compound of formula (VIII) in which A, R$_3$ and R$_4$ have the aboveindicated meanings. The reaction can be written:

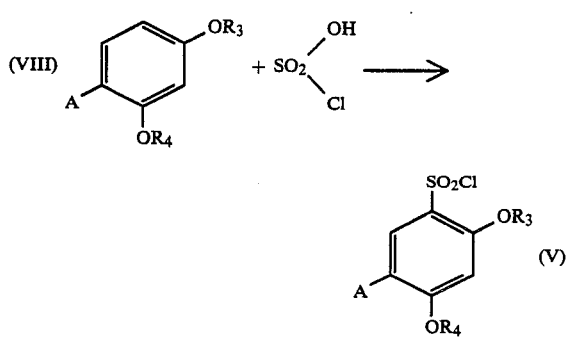

The hydrochloride of the compounds of formula (I) can be obtained by the reaction of an amine of formula (XI):

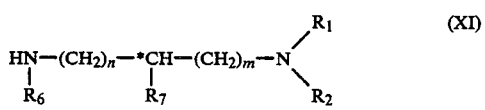

in which:
n and m independently from each other take values from 1 to 4,
$R_1$, $R_2$, $R_6$ and $R_7$ have the aboveindicated meanings, on a sulfochloride of formula (V):

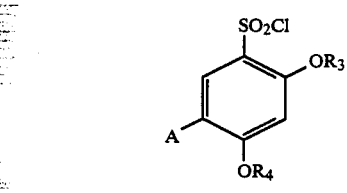

in which:
$R_3$ and $R_4$ have the aboveindicated meanings and
A has any one of the aboveindicated meanings for $R_5$ with the exception of the $NH_2$ group (it being understood that another halogenate of the compounds of the formula (I), is obtained if another sulfohalide is utilized, for example, a sulfobromide, instead and in place of the abovesaid sulfochloride).

The production of compounds of formula (I) in which $R_5$ represents $NH_2$, is carried out by reducing the compound of formula (I) in which $R_5$ represents $NO_2$ by catalytic hydrogenation or by chemical reduction.

The hydrochloride of the compounds of formula (I) obtained as has just been indicated has the formula:

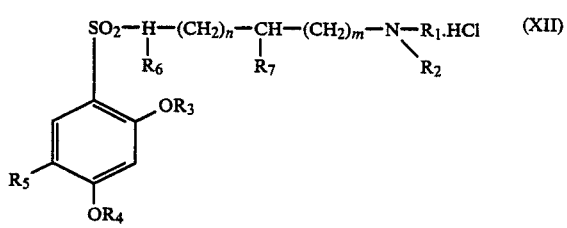

The passage from the hydrochloride of formula (XII) indicated above to the unsalted compound of formula (I), that is to say in the form of base, can be done in solution, by the reaction with a strong base such as sodium hydroxide, or potassium hydroxide, or any other base having an equivalent basic character.

Conversion of the hydrochloride of formula (XII) into a different salt can be effected by passing through the base of formula (I) and then by salifying the latter according to conventional processes.

A preferred group of amines used in the preparation of the compounds of formula (I), or of their corresponding salts, is constituted by the following:
dimethylamino-ethylamine,
diethylamino-ethylamine,
pyrrolidino-ethylamine,
piperidino-ethylamine,
morpholino-ethylamine,
dimethylamino-propylamine,
diethylamino-propylamine,
piperidino-propylamine,
3-(2-methyl piperidino)propylamine,
morpholino-propylamine.

The following examples, relating to the preparation of a certain number of sulfochlorides and new benzenesulfonamides serve to illustrate the invention, but are not limiting.

EXAMPLE 1

Preparation of 2,4-dimethoxy benzenesulfonyl chloride

This is carried out in two steps, following the technique of C. M. SUTER and H. L. HANSEN reported in J. of Am. Chem. Soc. 1933, 55, 2080.

1st step: Preparation of potassium 2,4-dimethoxy benzenesulfonate 85 g (0.615 mole) of 1,3-dimethoxy benzene are placed into a triple-necked flask of 250 cm$^3$, provided with a thermometer, with a dropping funnel and with a magnetic stirring system. After cooling to about 0° C., 50 cm$^3$ (0.9 mole) of sulfuric acid (d=1.83–1.84) were added drop by drop. The mixture was then brought to room temperature and left to stand 1.5 h. The reaction mixture set solid, was poured into 750 cm$^3$ of a saturated solution of potassium carbonate (138 g/l), then left to stand overnight. The precipitate obtained was filtered then dried under phosphoric vacuum.

Yield 79%.

2nd step: Conversion to 2,4-dimethoxy benzenesulfonyl chloride

Successively 124 g (0.484 mole) of potassium 2,4-dimethoxy benzenesulfonate and 500 cm$^3$ of dimethylformamide were introduced into a triple-necked flask of one liter, provided with a stirring system and a calcium chloride trap. To the suspension obtained were added drop by drop and at room temperature 69.5 g (0.583 mole) of thionyl chloride. After standing overnight, the mixture was poured onto crushed ice. The white precipitate obtained was drained, washed abundantly with water then dried under phosphoric vacuum.

Yield 75% mp 72° C. (litt. 70.5° C.).

EXAMPLE 2

Preparation of 2,4,5-trimethoxy benzenesulfonyl chloride

This may be carried out according to two methods:

1st method

Into a triple-necked flask of 500 cm$^3$, provided with a thermometer, with a dropping funnel, with a calcium chloride trap and a magnetic stirring system, were placed 42 g (0.25 mole) of 1,2,4-trimethoxy benzene in solution in 200 cm³ of pure chloroform. The reaction medium, placed under a nitrogen atmosphere and cooled to −10° C., were added drop by drop 80 cm³ of chlorosulfonic acid. Successively a creamy white milky precipitate was formed, then a greenish solution with changes to brown. When the addition was ended, the reaction medium was left to stand 1 h at ambient temperature, then poured over crushed ice. The precipitate obtained was extracted with chloroform; the organic phase was then dried over sodium sulfate and then evaporated under reduced pressure. The brown residue formed was washed with a minimum of toluene until the obtaining of a beige solid which was then chromatographed on a silica column.

Elution with benzene, then with a benzene-chloroform mixture (50-50) gave the 2,4,5-trimethoxy benzenesulfonyl chloride.

Yield 26% mp 147° C.

NMR (CDCl₃) at 80 MHz: δ 7.29 ppm (s 1H ArH); δ6.55 ppm (s 1H ArH); δ 3.93, 3.78 and 3.53 ppm (3s 9H OCH₃)

IR (KBr) ν SO₂, as 1350 cm⁻¹, s 1160 cm⁻¹.

2nd method

It comprises 4 steps:

3,4-dimethoxy chlorobenzene:

Into a triple-necked flask of a liter, provided with a magnetic stirring system, with a thermometer, with a calcium chloride trap and with a dropping funnel, were introduced into the cold at about 0° C. and successively 138 g (1 mole) of veratrol then drop by drop 135 g (1 mole) of sulfuryl chloride. When the addition was terminated, the reaction medium was brought to room temperature, then after standing one hour was distilled under reduced pressure.

Yield 83% b.p.: 120° C. under 1 999,83 Pa (15 mm Hg)

4,5-dimethoxy 2-nitro chlorobenzene:

Into a triple-necked flask of one liter, provided with a magnetic stirring system, with a thermometer and a dropping funnel, were introduced successively 143.9 g (0.83 mole) of 3,4-dimethoxy chlorobenzene, then drop by drop 166 cm³ of nitric acid (d=1.38), without the temperature exceeding 25° C. When the addition was ended, the reaction mixture was allowed to stand 1.5 h and then filtered.

Yield 95% mp 105° C.

2,4,5-trimethoxy nitrobenzene:

Into a two liter flask, provided with a cooling device, were introduced successively a solution of methanolic potash (100 g of KOH and 500 cm³ of methanol), then 100 g (0.46 mole) of 4,5-dimethoxy 2-nitro chlorobenzene and carborundum. The mixture was brought to boiling under reflux for 6 h. After cooling, the reaction medium was filtered; the precipitate obtained was washed with methanol.

Yield 95% mp 129° C.

2,4,5-trimethoxy aniline:

Into a 500 cm³ flask, provided with a cooling device, were added successively 21.3 g (0.1 mole) of 2,4,5-trimethoxy nitrobenzene, 80 g of chemically pure stannous chloride for mirror making, 100 cm³ of a hydrochloric acid solution (d=1.18) and carborundum. The mixture was brought to boiling under reflux for 1 h. After cooling, a caustic soda solution was added until the precipitate disolved. The solution obtained was extracted with methylene chloride. The organic extracts were dried over sodium sulfate then evaporated under reduced pressure. The residue obtained was crystallized in ethanol.

Yield 80% mp 94° C.

2,4,5-trimethoxy benzenesulfonyl chloride:

Into a triple-necked flask of 250 cm³, provided with a stirring system and a thermometer, were introduced 18.3 g (0.1 mole of 2,4,5-trimethoxy aniline then 50 cm³ of a hydrochloric acid solution (d=1.18). After standing for 4 hours, the amine was diazotized at −5° C. by the addition of a sodium nitrite solution (10 g of NaNO₂ in 50 cm³ of water). The diazonium salt obtained was poured slowly into a triple-necked flask, heated to 40° C. and under a nitrogen atmosphere, containing 200 cm³ of acetic acid saturated with sulfur dioxide and 7 g of cupric chloride. The mixture was brought for 2 h to 60° C., then poured on to crushed ice.

Yield 35% mp 147° C.

EXAMPLE 3

Preparation of 5-chloro 2,4-dimethoxy benzenesulfonyl chloride

It was carried out in 2 steps from 1,3-dimethoxy benzene:

1st step: Preparation of 2,4-dimethoxy chlorobenzene

Procedure was according to the technique of G. CASTELFRANCHI and G. BORRA reported in Annali di Chimica, 1953, 43, 293.

Into a triple-necked flask of 500 cm³, provided with a magnetic stirring system, with a thermometer, with a calcium chloride trap and a dropping funnel, and cooled to 10° C., were introduced successively 97.5 (0.70 mole) of 1,3-dimethoxy benzene and then drop by drop 96.5 g (0.70 mole) of sulfuryl chloride. Once the addition was ended, the solution was brought back to ambient temperature and allowed to stand 2 h and then distilled.

Yield 85% b.p. 137° C. under 2 399,80 Pa (18 mm Hg).

2nd step: Conversion to 5-chloro 2,4-dimethoxy benzenesulfonyl chloride

Into a triple-necked flask of 500 cm³, provided with a magnetic stirring system, with a calcium chloride trap, a thermometer and a dropping funnel, were introduced 35 g (0.2 mole) of 2,4-dimethoxy chlorobenzene in solution in 250 cm² of pure chloroform. The solution was cooled to 0° C., then supplemented drop by drop with 50 cm³ (0.75 mole) of chlorosulfonic acid. Once the addition was ended, the reaction medium was brought to ambient temperature, then left to stand 3 h; it was then poured over crushed ice. The mixture obtained was extracted with chloroform. The organic extracts were dried over sodium sulfate then concentrated to crystallization. The solid obtained was recrystallized in an ethyl ether/benzene mixture.

Yield 74% mp 175° C.

NMR (CDCl₃) at 80 MHz: δ 7.87 ppm (S 1H ArH); δ 6.55 ppm (s 1H ArH); δ 4 and 3.96 ppm (2s 6H OCH₃)

IR (KBr): ν SO₂, as 1385 cm⁻¹, s 1170 cm⁻¹.

EXAMPLE 4

Preparation of 5-bromo 2,4-dimethoxy benzenesulfonyl chloride

This was carried out in 2 steps starting from 1,3-dimethoxy benzene:

1st step: Preparation of 2,4-dimethoxy bromobenzene

This was done according to the procedure of S. T. FENG and K. Y. CHIU reported in Hsueh Pao, 1959, 25, 277.

Into a triple-necked flask of 250 cm³, provided with a magnetic stirring system, with a thermometer, and cooled to 10° C., were added successively 27.6 g (0.2 mole) of 1,3-dimethoxy benzene then in small portions 36 g (0.2 mole) of N-bromosuccinimide. Once the addition was ended, the reaction medium was brought to ambient temperature and left to stand 2 h. After washing with water and extraction with chloroform, the organic extracts were dried over sodium sulfate then concentrated under reduced pressure. The residual liquid was distilled.

Yield 82% b.p.: 150° C. under 1 999,83 Pa (15 mm Hg).

2nd step: Conversion to 5-bromo 2,4-dimethoxy benzenesulfonyl chloride

It was obtained according to the same procedure as that described in Example 3 to prepare 5-chloro 2,4-dimethoxy benzenesulfonyl chloride. By using 65.1 g (0.3 mole) of 2,4-dimethoxy bromobenzene and 100 cm³ of chlorosulfonic acid, the yield was 77%. mp 195° C.

NMR (CDCl₃) at 60 MHz: δ 7.85 ppm (s 1H ArH); δ 6.70 ppm (s 1H ArH); δ 3.92 and 3.88 ppm (2s 6H OCH₃);

IR (KBr): ν SO₂, as 1385 cm⁻¹, s 1165 cm⁻¹.

EXAMPLE 5

5-alkylsulfonyl 2,4-dimethoxy benzenesulfonyl chlorides

They were obtained from the 2,4-dimethoxy benzenesulfonyl chlorides described in Example 1. The general diagram for their preparation is as follows:

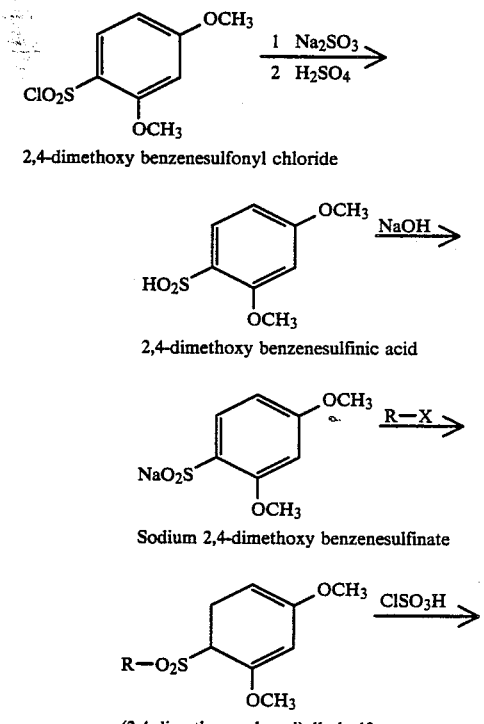

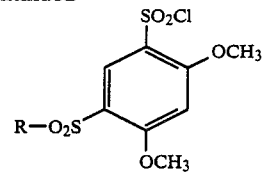

5-alkylsulfonyl 2,4-dimethoxy benzenesulfonyl chloride

2,4-dimethoxy benzenesulfinic acid

To an aqueous solution containing 129 g (0.974 mole) of sodium sulfite were added in small amounts and with stirring 115 g (0.487 mole) of 2,4-dimethoxy benzenesulfonyl chloride. During this operation, the pH was kept alkaline by the addition of caustic soda. After standing for 3 h, the reaction medium was filtered. The filtrate was acidified with 2N sulfuric acid until the precipitation of the sulfinic acid.

Yield 72% mp 122° C.

Sodium 2,4-dimethoxy benzenesulfinate

This was obtained by the addition of the stoichiometric amount of sodium hydroxide in aqueous solution. The sulfinate solution was evaporated to dryness.

(2,4-dimethoxy phenyl)alkylsulfones

General procedure

Into a 500 cm³ flask, provided with a cooling system and a magnetic stirring system, were added successively 0.1 mole of sodium 2,4-dimethoxy benzenesulfonate, 250 cm³ of isopropanol, and then 0.15 mole of alkyl halide, preferably an iodide. The mixture was brought to boiling under reflux 5 to 30 h according to the halide used. After cooling, the reaction medium was evaporated to dryness. The residue was taken up again in water and then extracted with chloroform. The evaporation of the organic phase, after drying over sodium sulfate gave an oil which was crystallized in benzene.

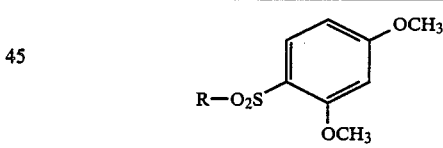

| R | MW | Time of heating | MP °C. | Yield % |
|---|---|---|---|---|
| CH₃ | 216 | 5 h | 109 | 65 |
| C₂H₅ | 230 | 7 h | 94 | 70 |
| nC₃H₇ | 244 | 15 h | 70 | 90 |
| iC₃H₇ | 244 | 30 h | 100 | 64 |

5-alkylsulfonyl 2,4-dimethoxy benzenesulfonyl chlorides

General procedure

Into a triple-necked flask of one liter, provided with a magnetic stirring system, with a calcium chloride trap, with a thermometer and a dropping funnel, was introduced a solution of (2,4-dimethoxy-phenyl)alkylsulfone (0.2 mole) in 200 cm³ of pure chloroform. After cooling to −10° C., 100 cm³ of chlorosulfonic acid were added drop by drop. Once the addition was ended, the mixture was left to stand 0.5 h at −10° C., then brought back to room temperature and left with stirring for 7 h; it was then poured over crushed ice. The mixture obtained was extracted with chloroform. The organic phase was dried over sodium sulfate, filtered, then evaporated under reduced pressure. The residue was crystallized in benzene.

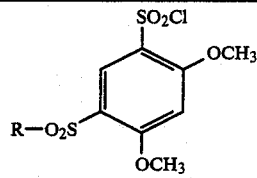

| R | MW | MP °C. | Yield % |
|---|---|---|---|
| CH$_3$ | 314.5 | 204 | 52 |
| C$_2$H$_5$ | 328.5 | 191 | 77 |
| nC$_3$H$_7$ | 342.5 | 169 | 87 |
| iC$_3$H$_7$ | 342.5 | 218 | 66 |

2,4-dimethoxy 5-methylsulfonyl benzenesulfonyl chloride

NMR (DMSO) at 80 MHz: δ 8.2 ppm (s 1H ArH); δ 6.9 ppm (s 1H ArH); δ 4.1 ppm and 4.05 ppm (2s 6H OCH$_3$); 3.2 ppm (s 3H CH$_3$).

IR (KBr): ν SO$_2$—Cl, as 1360 cm$^{-1}$, s 1170 cm$^{-1}$; ν SO$_2$—CH$_3$, as 1300 cm$^{-1}$, s 1140 cm$^{-1}$.

5-ethylsulfonyl 2,4-dimethoxy benzenesulfonyl chloride

NMR (DMSO) at 80 MHz: δ 8.2 ppm (s 1H ArH); δ 6.93 ppm (s 1H ArH); δ 4.15 ppm and 4.1 ppm (2s 6H OCH$_3$); δ 3.24 ppm (q 2H —CH$_2$—); δ 1.18 ppm (t 3H CH$_3$—).

IR (KBr): ν SO$_2$—Cl, as 1370 cm$^{-1}$, s 1175 cm$^{-1}$; ν SO$_2$—CH$_2$—, as 1315 cm$^{-1}$, s 1140 cm$^{-1}$.

2,4-dimethoxy 5-propylsulfonyl benzenesulfonyl chloride

NMR (DMSO) at 80 MHz: δ 8.05 ppm (s 1H ArH); δ 6.72 ppm (s 1H ArH); 3.92 and 3.87 ppm (2s 6H OCH$_3$); δ 3.2 ppm (t 2H—CH$_2$—SO$_2$—); δ 1.45 ppm (m 2H—CH$_2$—); δ 0.85 ppm (t 3H CH$_3$).

IR (KBr): ν SO$_2$Cl, as 1370 cm$^{-1}$, s 1180 cm$^{-1}$; ν SO$_2$—CH$_2$, as 1315 cm$^{-1}$, s 1135 cm$^{-1}$.

5-isopropylsulfonyl 2,4-dimethoxy benzenesulfonyl chloride

NMR (DMSO) at 80 MHz: δ 8.02 ppm (s 1H ArH); δ 6.7 ppm (s 1H ArH); δ 3.92 and 3.85 ppm (2s 6H OCH$_3$); δ 3.48 ppm (m 1H

δ 1.11 and 1.03 ppm (2s 6H CH$_3$).

IR (KBr): ν SO$_2$—Cl, as 1365 cm$^{-1}$, s 1175 cm$^{-1}$; ν SO$_2$—CH, as 1300 cm$^{-1}$, s 1130 cm$^{-1}$.

EXAMPLE 6

Preparation of substituted 2,4-dimethoxy benzenesulfonamides

To 0.015 mole of benzenesulfonyl chloride in solution in a mixture of methylene chloride (40 cm$^3$) and methanol (10 cm$^3$), was added 0.015 mole of dialkylaminoalkylamine in solution in 10 cm$^3$ of methylene chloride. After standing 2 h, with stirring and at room temperature, the reaction medium was evaporated to dryness and then taken up again in 50 cm$^3$ of water. The aqueous solution was washed with ethyl ether, then evaporated to dryness. The residue was crystallized in an isopropanol/methanol mixture. Possible conversion to the base was carried out by treating the aqueous solution of the hydrochloride with N soda until precipitation. The precipitate was extracted with methylene chloride. The organic solution was dried then evaporated under reduced pressure. The base obtained was crystallized in an ethyl ether/petroleum ether mixture.

Other compounds were prepared similarly and are assembled in the following Table I (the melting point indicated for each compound is, except for indication to the contrary, that of the hydrochloride).

TABLE I

COMPOUND OF FORMULA

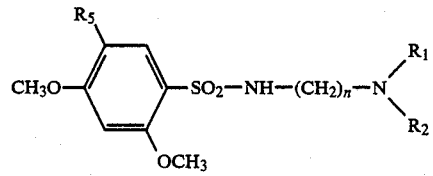

| Product no | N(R$_1$)(R$_2$) | n | R$_5$ | Formula of compound in hydrochloride form | Molecular weight | Melting point of hydrochloride | Yield % |
|---|---|---|---|---|---|---|---|
| 880 | N(CH$_3$)(CH$_3$) | 2 | Cl | C$_{12}$H$_{20}$Cl$_2$N$_2$O$_4$S | 359 | 237 | 78 |
| 881 | N(C$_2$H$_5$)(C$_2$H$_5$) | 2 | Cl | C$_{14}$H$_{24}$Cl$_2$N$_2$O$_4$S | 387 | 202 | 93 |

TABLE I-continued
COMPOUND OF FORMULA
| Product no | NR₁R₂ | n | $R_5$ | Formula of compound in hydrochloride form | Molecular weight | Melting point of hydrochloride | Yield % |
|---|---|---|---|---|---|---|---|
| 882 |  | 2 | Cl | $C_{14}H_{22}Cl_2N_2O_4S$ | 385 | 209 | 83 |
| 883 |  | 2 | Cl | $C_{15}H_{24}Cl_2N_2O_4S$ | 399 | 220 | 83 |
| 884 |  | 2 | Cl | $C_{14}H_{22}Cl_2N_2O_5S$ | 401 | 232 | 82 |
| 886 | N(CH₃)₂ | 3 | Cl | $C_{13}H_{22}Cl_2N_2O_4S$ | 373 | 203 | 89 |
| 887 | N(C₂H₅)₂ | 3 | Cl | $C_{15}H_{26}Cl_2N_2O_4S$ | 401 | 179 | 60 |
| 888 |  | 3 | Cl | $C_{16}H_{26}Cl_2N_2O_4S$ | 413 | 191 | 85 |
| 889 |  | 3 | Cl | $C_{15}H_{24}Cl_2N_2O_5S$ | 415 | 212 | 61 |
| 897 | N(CH₃)₂ | 2 | OCH₃ | $C_{13}H_{23}ClN_2O_5S$ | 354.5 | 247 | 90 |
| 898 | N(C₂H₅)₂ | 2 | OCH₃ | $C_{15}H_{27}ClN_2O_5S$ | 382.5 | 194 | 76 |
| 899 |  | 2 | OCH₃ | $C_{15}H_{25}ClN_2O_5S$ | 380.5 | 186 | 89 |
| 900 |  | 2 | OCH₃ | $C_{16}H_{27}ClN_2O_5S$ | 394.5 | 207 | 66 |

TABLE I-continued

COMPOUND OF FORMULA

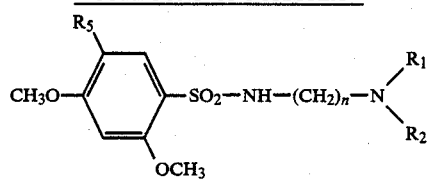

| Product no | $\begin{array}{c} R_1 \\ N \\ R_2 \end{array}$ | n | $R_5$ | Formula of compound in hydrochloride form | Molecular weight | Melting point of hydrochloride | Yield % |
|---|---|---|---|---|---|---|---|
| 901 | N─O (morpholino) | 2 | $OCH_3$ | $C_{15}H_{25}ClN_2O_6S$ | 396.5 | 220 | 48 |
| 893 | $N(CH_3)_2$ | 3 | $OCH_3$ | $C_{14}H_{25}ClN_2O_5S$ | 368.5 | 212 | 57 |
| 891 | $N(C_2H_5)_2$ | 3 | $OCH_3$ | $C_{16}H_{29}ClN_2O_5S$ | 396.5 | 173 | 86 |
| 894 | piperidino | 3 | $OCH_3$ | $C_{17}H_{29}ClN_2O_5S$ | 408.5 | 236 | 56 |
| 895 | morpholino | 3 | $OCH_3$ | $C_{16}H_{27}ClN_2O_6S$ | 410.5 | 225 | 51 |
| 924 | $N(CH_3)_2$ | 2 | Br | $C_{12}H_{20}BrClN_2O_4S$ | 403.71 | 244 | 49 |
| 925 | $N(C_2H_5)_2$ | 2 | Br | $C_{14}H_{24}BrClN_2O_4S$ | 431.77 | 202 | 48 |
| 926 | pyrrolidino | 2 | Br | $C_{14}H_{22}BrClN_2O_4S$ | 429.75 | 226 | 64 |
| 927 | piperidino | 2 | Br | $C_{15}H_{24}BrClN_2O_4S$ | 443.78 | 204 | 71 |
| 928 | morpholino | 2 | Br | $C_{14}H_{22}BrClN_2O_5S$ | 445.75 | 246 | 71 |
| 930 | $N(CH_3)_2$ | 3 | Br | $C_{13}H_{22}BrClN_2O_4S$ | 417.74 | 227 | 85 |

TABLE I-continued

COMPOUND OF FORMULA $$\text{CH}_3\text{O} - \underset{\underset{\text{OCH}_3}{|}}{\overset{\overset{R_5}{|}}{\bigcirc}} - \text{SO}_2-\text{NH}-(\text{CH}_2)_n-\text{N}\underset{R_2}{\overset{R_1}{\diagdown}}$$

| Product no | $\text{N}\underset{R_2}{\overset{R_1}{\diagdown}}$ | n | $R_5$ | Formula of compound in hydrochloride form | Molecular weight | Melting point of hydrochloride | Yield % |
|---|---|---|---|---|---|---|---|
| 931 | $\text{N}(\text{C}_2\text{H}_5)_2$ | 3 | Br | $C_{15}H_{26}BrClN_2O_4S$ | 445.79 | 190 | 60 |
| 932 | piperidino | 3 | Br | $C_{16}H_{26}BrClN_2O_4S$ | 457.80 | 200 | 60 |
| 933 | morpholino | 3 | Br | HCl, $C_{15}H_{24}BrClN_2O_5S$<br>base $C_{14}H_{23}BrN_2O_5S$ | 459.77 | 237<br>127 | 72 |
| 955 | $\text{N}(\text{CH}_3)_2$ | 2 | $SO_2CH_3$ | $C_{13}H_{23}N_2O_6S_2Cl$ | 402.897 | 233 | 63 |
| 956 | $\text{N}(\text{C}_2\text{H}_5)_2$ | 2 | $SO_2CH_3$ | $C_{15}H_{27}N_2O_6S_2Cl$ | 430.951 | 211 | 70 |
| 957 | pyrrolidino | 2 | $SO_2CH_3$ | $C_{15}H_{25}N_2O_6S_2Cl$ | 428.935 | 232 | 62 |
| 958 | piperidino | 2 | $SO_2CH_3$ | $C_{16}H_{27}N_2O_6S_2Cl$ | 442.962 | 248 | 60 |
| 959 | morpholino | 2 | $SO_2CH_3$ | $C_{15}H_{25}N_2O_7S_2Cl$ | 444.932 | 246 | 66 |
| 961 | $\text{N}(\text{CH}_3)_2$ | 3 | $SO_2CH_3$ | $C_{14}H_{25}N_2O_6S_2Cl$ | 416.924 | 208 | 58 |
| 962 | $\text{N}(\text{C}_2\text{H}_5)_2$ | 3 | $SO_2CH_3$ | $C_{16}H_{29}N_2O_6S_2Cl$ | 444.978 | 220 | 65 |
| 963 | piperidino | 3 | $SO_2CH_3$ | $C_{17}H_{29}N_2O_6S_2Cl$ | 456.989 | 250 | 58 |

TABLE I-continued

COMPOUND OF FORMULA $$\text{CH}_3\text{O}-\underset{\underset{\text{OCH}_3}{|}}{\overset{\overset{R_5}{|}}{C_6H_3}}-SO_2-NH-(CH_2)_n-N\underset{R_2}{\overset{R_1}{<}}$$

| Product no | $N\overset{R_1}{\underset{R_2}{<}}$ | n | $R_5$ | Formula of compound in hydrochloride form | Molecular weight | Melting point of hydrochloride | Yield % |
|---|---|---|---|---|---|---|---|
| 964 | N-morpholino | 3 | $SO_2CH_3$ | $C_{16}H_{27}N_2O_7S_2Cl$ | 458.959 | 237 | 64 |
| 979 | $N(CH_3)_2$ | 2 | $SO_2C_2H_5$ | $C_{14}H_{25}ClN_2O_6S_2$ | 416.924 | 235 | 72 |
| 980 | $N(C_2H_5)_2$ | 2 | $SO_2C_2H_5$ | $C_{16}H_{29}ClN_2O_6S_2$ | 444.978 | 242 | 71 |
| 981 | N-pyrrolidino | 2 | $SO_2C_2H_5$ | $C_{16}H_{27}ClN_2O_6S_2$ | 442.962 | 246 | 73 |
| 982 | N-piperidino | 2 | $SO_2C_2H_5$ | $C_{17}H_{29}ClN_2O_6S_2$ | 456.989 | 247 | 63 |
| 983 | N-morpholino | 2 | $SO_2C_2H_5$ | $C_{16}H_{27}ClN_2O_7S_2$ | 458.959 | 243 | 44 |
| 985* | $N(CH_3)_2$ | 3 | $SO_2C_2H_5$ | $C_{15}H_{26}N_2O_6S_2$* | 394.490* | 170* | 60 |
| 986 | $N(C_2H_5)_2$ | 3 | $SO_2C_2H_5$ | $C_{17}H_{31}ClN_2O_6S_2$ | 459 | 176 | 80 |
| 987 | N-piperidino | 3 | $SO_2C_2H_5$ | $C_{18}H_{31}ClN_2O_6S_2$ | 471 | 203 | 42 |
| 988 | N-morpholino | 3 | $SO_2C_2H_5$ | $C_{17}H_{29}ClN_2O_7S_2$ | 472.986 | 204 | 70 |
| 1072 | N-(3-methylpiperidino) | 3 | $SO_2C_2H_5$ | $C_{19}H_{33}ClN_2O_6S$ | 485.043 | 170 | 83 |

TABLE I-continued

COMPOUND OF FORMULA $$CH_3O-\text{[benzene with }R_5\text{ top, }OCH_3\text{ bottom]}-SO_2-NH-(CH_2)_n-N(R_1)(R_2)$$

| Product no | $\mathrm{N}(R_1)(R_2)$ | n | $R_5$ | Formula of compound in hydrochloride form | Molecular weight | Melting point of hydrochloride | Yield % |
|---|---|---|---|---|---|---|---|
| 1061 | $N(CH_3)_2$ | 2 | H | $C_{12}H_{21}ClN_2O_4S$ | 324.82 | 204 | 72 |
| 1062 | $N(C_2H_5)_2$ | 2 | H | $C_{14}H_{25}ClN_2O_4S$ | 352.87 | 154 | 69 |
| 1063 | pyrrolidino | 2 | H | $C_{14}H_{23}ClN_2O_4S$ | 350.85 | 125 | 87 |
| 1064 | piperidino | 2 | H | HCl, $C_{15}H_{25}ClN_2O_4S$<br>base $C_{15}H_{24}N_2O_4S$ | 364.88<br>328.42 | 164<br>108 | 77 |
| 1065 | morpholino | 2 | H | HCl, $C_{14}H_{23}ClN_2O_5S$<br>base $C_{14}H_{22}N_2O_5S$ | 366.85<br>330.39 | 179<br>122 | 60 |
| 1067 | $N(CH_3)_2$ | 3 | H | HCl, $C_{13}H_{22}ClN_2O_4S$ | 337.83 | 157 | 65 |
| 1068 | $N(C_2H_5)_2$ | 3 | H | HCl, $C_{15}H_{27}ClN_2O_4S$<br>base $C_{15}H_{26}N_2O_4S$ | 366.90<br>330.44 | 141<br>55 | 78 |
| 1069 | piperidino | 3 | H | HCl, $C_{16}H_{27}ClN_2O_4S$<br>base $C_{16}H_{26}N_2O_4S$ | 378.91<br>342.45 | 166<br>86 | 78 |
| 1070 | morpholino | 3 | H | $C_{15}H_{25}ClN_2O_5S$ | 380.88 | 195 | 45 |
| 1071 | 3-methylpiperidino | 3 | H | $C_{17}H_{29}ClN_2O_4S$ | 392.94 | 176 | 50 |
| 1094 | $N(CH_3)_2$ | 2 | $SO_2-nC_3H_7$ | $C_{15}H_{27}ClN_2O_6S_2$ | 430.95 | 163 | 73 |

TABLE I-continued

COMPOUND OF FORMULA $$\text{CH}_3\text{O}-\underset{\underset{\text{OCH}_3}{|}}{\overset{\overset{R_5}{|}}{\bigcirc}}-\text{SO}_2-\text{NH}-(\text{CH}_2)_n-\text{N}\overset{R_1}{\underset{R_2}{\diagdown}}$$

| Product no | $\text{N}\overset{R_1}{\underset{R_2}{\diagdown}}$ | n | $R_5$ | Formula of compound in hydrochloride form | Molecular weight | Melting point of hydrochloride | Yield % |
|---|---|---|---|---|---|---|---|
| 1095 | $\text{N}(\text{C}_2\text{H}_5)_2$ | 2 | $SO_2-{}_nC_3H_7$ | $C_{17}H_{31}ClN_2O_6S_2$ | 459 | 224 | 91 |
| 1096 | pyrrolidinyl | 2 | $SO_2-{}_nC_3H_7$ | $C_{17}H_{29}ClN_2O_6S_2$ | 456.99 | 206 | 71 |
| 1097 | piperidinyl | 2 | $SO_2-{}_nC_3H_7$ | $C_{18}H_{31}ClN_2O_6S_2$ | 471.02 | 226 | 89 |
| 1098 | morpholinyl | 2 | $SO_2-{}_nC_3H_7$ | $C_{17}H_{29}ClN_2O_7S_2$ | 472.99 | 186 | 83 |
| 1100* | $\text{N}(\text{CH}_3)_2$ | 3 | $SO_2-{}_nC_3H_7$ | $C_{16}H_{28}N_2O_6S_2$ base | 408.517 | 158* | 69 |
| 1101 | $\text{N}(\text{C}_2\text{H}_5)_2$ | 3 | $SO_2-{}_nC_3H_7$ | $C_{18}H_{33}ClN_2O_6S_2$ | 473.03 | 158 | 65 |
| 1102* | morpholinyl | 3 | $SO_2-{}_nC_3H_7$ | $C_{18}H_{30}N_2O_7S_2$ base<br>HCl, $C_{18}H_{31}ClN_2O_7S_2$ | 450.55<br>487.01 | 122<br>150 | 68 |
| 1103 | 3-methylpiperidinyl | 3 | $SO_2-{}_nC_3H_7$ | $C_{20}H_{35}ClN_2O_6S_2$ | 499.07 | 167 | 71 |
| 1104 | $\text{N}(\text{CH}_3)_2$ | 2 | $SO_2-iC_3H_7$ | HCl, $C_{15}H_{27}ClN_2O_6S_2$ | 430.95 | 217 | 71 |
| 1105 | $\text{N}(\text{C}_2\text{H}_5)_2$ | 2 | $SO_2-iC_3H_7$ | $C_{17}H_{31}ClN_2O_6S_2$ | 459 | 201 | 84 |
| 1106 | pyrrolidinyl | 2 | $SO_2-iC_3H_7$ | $C_{17}H_{29}ClN_2O_6S_2$ | 456.99 | 222 | 77 |

TABLE I-continued

COMPOUND OF FORMULA

| Product no | $\begin{array}{c}R_1\\ N\\ R_2\end{array}$ | n | $R_5$ | Formula of compound in hydrochloride form | Molecular weight | Melting point of hydrochloride | Yield % |
|---|---|---|---|---|---|---|---|
| 1107 |  | 2 | $SO_2-iC_3H_7$ | $C_{18}H_{31}ClN_2O_6S_2$ | 471.02 | 239 | 91 |
| 1108 | 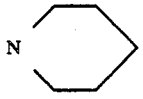 | 2 | $SO_2-iC_3H_7$ | $C_{17}H_{29}ClN_2O_7S_2$ | 472.99 | 198 | 83 |
| 1110 |  | 3 | $SO_2-iC_3H_7$ | $C_{16}H_{29}ClN_2O_6S_2$ | 444.98 | 162 | 68 |
| 1111 |  | 3 | $SO_2-iC_3H_7$ | $C_{18}H_{33}ClN_2O_6S_2$ | 473.08 | 172 | 94 |
| 1112 |  | 3 | $SO_2-iC_3H_7$ | $C_{18}H_{31}ClN_2O_7S_2$ | 487.01 | 185 | 68 |
| 1113 | 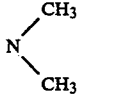 | 3 | $SO_2-iC_3H_7$ | $C_{20}H_{35}ClN_2O_6S_2$ | 499.07 | 200 | 65 |

*Results are relative to the compound which is in the form of its base.

The new benzenesulfonamides according to the invention, as well as their physiologically acceptable organic or inorganic salts, have remarkable pharmacological properties.

The compounds according to the invention exert a control action on the central nervous system and particularly a psychomodulator reaction. They can act particularly, either as antidepressant agents, or as tranquilizing anxiolytic agents. The activity of these compounds is reinforced by the lipophile nature of the molecule, due to the presence of an alkoxy group on the aromatic nucleus at the 4 position.

The compounds according to the invention are also distinguished by the fact that they potentiate pentobarbital sleep, that they have little or no affinity for the dopaminergic sites usually recognized as associated with certain undesirable effects (galactorrea, amenorrhea, extrapyramidal syndromes), and that they are devoid of toxicity.

Their therapeutic index is compatible with their use as a medicament.

The compounds are advantageously introduced as the active principle in the treatment of diseases with depressive, anxiety components and causing in particular psychosomatic disorders.

The compounds according to the invention are for this purpose packaged with excipients and traditional adjuvants, particularly those used for the preparation of tablets, powders, capsules, drinkable ampoules and injectable solutions.

The administration of medicaments containing the compounds according to the invention is carried out preferably orally, parenterally, rectally or topically and the doses of active compound administered are preferably comprised between 10 and 700 mg and particularly between 50 and 500 mg/day.

By way of example, different tests for the establishing of the pharmacological properties of the compounds according to the invention are reported below.

TESTS RELATING TO STUDY OF THE INTERACTIONS OF THE MEDICAMENTS ACCORDING TO THE INVENTION WITH PENTOBARBITAL

The tests were warried out on EOPS SWISS mice of male sex, weighing from 20 to 24 g, coming from the breeding center of LE GENEST.

The animals were acclimatized at least 8 days in the animal section of the laboratory before the tests.

The batches were of 10 mice per test and per product.

As reference products, to carry out control tests, the three following substances were used:

N-[(1-ethyl 2-pyrrolidinyl)methyl]2-methoxy 5-sulfamoyl benzamide known under the name sulpiride;

N-[(1-ethyl 2-pyrrolidinyl)methyl]2-methoxy 5-ethylsulfonyl benzamide known under the sultopride;

N-(2-diethylamino ethyl)2-methoxy 5-methylsulfonyl benzamide known under the tiapride.

The compounds according to the invention and the reference substances were administered in aqueous suspension in water with 3% of gum arabic for the oral route (tests of interactions with barbiturates).

The pharmacological reagent namely the pentobarbital was administered in solution in an isotonic NaCl solution.

The volumes administered were 0.5 ml of a solution with 1.6 g/l for 20 g of body weight intraperitoneally (40 mg/kg).

To carry out these tests, there were administered to these batches of 10 SWISS male mice, the compounds according to the invention or the reference products (namely sulpiride, sultopride or tiapride) orally at the dosage of 200 mg/kg. 60 minutes after ingestion of the compounds according to the invention or of the reference product, pentabarbital was administered to the animals in the sodium form such as that marketed under the trademark NEMBUTAL. Measurement was then made of:

the drowsiness time,
the sleeping time, and the percentage of variations over and under the sleeping time was measured. The results of these tests are shown in the following Table II.

TABLE II

| Product n° | Sleeping time (pentobarbital) mn | Variation % |
|---|---|---|
| 880 | | +55,6 |
| 881 | | +30,8 |
| 882 | 176 ± 21 | +144,4 |
| 883 | 176 ± 12 | +147,9 |
| 884 | 150 ± 24 | +111,3 |
| 886 | | +36,4 |
| 887 | | +24,7 |
| 888 | 140 ± 20 | +97,2 |
| 889 | 156 ± 15 | +119,7 |
| 897 | | −8,8 |
| 898 | | −15,4 |
| 899 | | +23,1 |
| 900 | | +14,3 |
| 901 | | +11,0 |
| 893 | | +3,3 |
| 891 | | −7,7 |
| 894 | | +12,1 |
| 895 | | +67,1 |
| 924 | | +16,5 |
| 925 | | +29,4 |
| 926 | 168 ± 30 | +133,3 |
| 927 | 169 ± 26 | +134,7 |
| 928 | 165 ± 24 | +129,2 |
| 930 | | +52,8 |

TABLE II-continued

| Product n° | Sleeping time (pentobarbital) mn | Variation % |
|---|---|---|
| 931 | | +28,6 |
| 932 | 142 ± 15 | +97,2 |
| 933 | 180 ± 32 | +150,0 |
| 955 | | +11,7 |
| 956 | | −26,4 |
| 957 | | +26,8 |
| 958 | | +16,9 |
| 959 | | +41,7 |
| 961 | | +15,6 |
| 962 | | +11,0 |
| 963 | | −5,2 |
| 964 | | +16,9 |
| 979 | | −8,5 |
| 980 | | +21,1 |
| 981 | | +9,1 |
| 982 | | +2,6 |
| 983 | | −5,2 |
| 985 | | +20,8 |
| 986 | | +16,9 |
| 987 | | +9,9 |
| 988 | | +9,9 |

The new trisubstituted benzenesulfonamides according to the invention constitute a class of product and a class of medicaments which is particularly preferred.

The disubstituted benzenesulfoamides have interesting properties, but taking into account the results obtained, it results that when $R_5$ is different from hydrogen, the biological properties of the trisubstituted benzenesulfoamides are amplified with respect to those of the corresponding disubstituted benzenesulfonamides.

Consequently, the combination of the disubstitution at (2,4), by alkoxy groups and the substitution at the 5 position is particularly favorable with respect to the overall activity of the molecules.

Study of the results obtained shows that the compounds according to the invention are psychomodulators. Those for which the percentage variation of the sleep time is greater than +50% are very distinct potentiators of pentobarbital sleep and consequently can be used as tranquilizers or anxiolytic agents.

The compounds according to the invention for which the percentage variation in sleep time varies from about 0% to about 50% are potentiators of activity in the neighborhood of the reference compounds sultopride and tiapride, used.

The compounds according to the invention for which the percentage variation in sleep time is less than 0% are antagonists and can be used as antidepressant agents.

It is noted that the sulpiride used as reference product shows itself to be either a potentiator, or an antagonist which shows its double profile of neuroleptic and antidepressant agent.

We claim:

1. A compound of the formula:

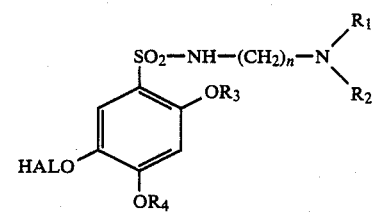

and the physiologically acceptable salts thereof, wherein n is 2 or 3;

R₃ and R₄ are lower alkyl,

R₁ and R₂ together with the nitrogen to which they are attached, represent a heterocyclic group selected from the group consisting of pyrrolidino, morpholino or piperidino, and wherein HALO is chloro or bromo.

2. The compound of claim 1 wherein n is 2.

3. The compound of claim 1 wherein HALO is chloro.

4. The compound of claim 1 which is selected from the group consisting of 2,4-dimethoxy-5-chloro-N-(2-N-pyrrolidinyl ethyl)benzenesulfonamide; 2,4-dimethoxy-5-chloro-N-(2-N-piperidinyl ethyl)benzenesulfnamide; 2,4-dimethoxy-5-chloro-N-(2-N-morpholinyl ethyl)benzenesulfonamide; 2,4-dimethoxy-5-chloro-N-(2-N-piperidinyl propyl)benzenesulfonamide; 2,4-dimethoxy-5-chloro-N-(2-N-morpholinyl propyl)benzenesulfonamide; 2,4-dimethoxy-5-bromo-N-(2-N-pyrrolidinyl ethyl)benzenesulfonamide; 2,4-dimethoxy-5-bromo-N-(2-N-piperidinyl ethyl)benzenesulfonamide; 2,4-dimethoxy-5-bromo-N-(2-N-morpholinyl ethyl)benzenesulfonamide; 2,4-dimethoxy-5-bromo-N-(2-N-piperidinyl-propyl)benzenesulfonamide; 2,4-N-dimethoxy-5-bromo-N-(2-N-morpholinyl-propyl)benzenesulfonamide.

5. The compound of claim 4 which is selected from the group consisting of 2,4-dimethoxy-5-chloro-N-(2-N-pyrrolidinyl ethyl)benzenesulfonamide; 2,4-dimethoxy-5-chloro-N-(2-N-piperidinyl ethyl)benzenesulfonamide; 2,4-dimethoxy-5-chloro-N-(2-N-morpholinyl ethyl)benzenesulfonamide; 2,4-dimethoxy-5-bromo-N-(2-N-pyrrolidinyl ethyl)benzenesulfonamide and 2,4-dimethoxy-5-bromo-N-(2-N-piperidinyl ethyl)benzenesulfonamide.

6. A pharmaceutical composition which comprises a pharmaceutical carrier and a phenobarbital sleep potentiating effective amount of a compound of the formula:

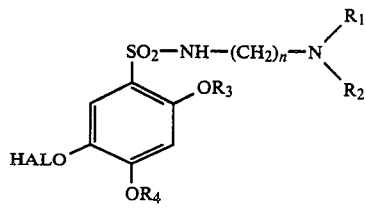

and the physiologically acceptable salts thereof, wherein n is 2 or 3;

R₃ and R₄ are lower alkyl;

R₁ and R₂ together with the nitrogen to which they are attached, represent a heterocyclic group selected from the group consisting of pyrrolidino, morpholino, or piperidino; and wherein HALO is chloro or bromo.

7. The pharmaceutical composition of claim 6 wherein n is 2.

8. The pharmaceutical composition of claim 6 wherein HALO is chloro.

9. The pharmaceutical composition of claim 6 wherein the compound is selected from the group consisting of 2,4-dimethoxy-5-chloro-N-(2-N-pyrrolidinyl ethyl)benzenesulfonamide; 2,4-dimethoxy-5-chloro-N-(2-N-piperidinyl ethyl)benzenesulfonamide; 2,4-dimethoxy-5-chloro-N-(2-N-morpholinyl)benzenesulfonamide; 2,4-dimethoxy-5-chloro-N-(2-N-piperidinyl propyl)benzenesulfonamide; 2,4-dimethoxy-5-chloro-N-(2-N-morpholinyl propyl)benzenesulfonamide; 2,4-dimethoxy-5-bromo-N-(2-N-pyrrolidinyl ethyl)benzenesulfonamide; 2,4-dimethoxy-5-bromo-N-(2-N-piperidinyl ethyl)benzenesulfonamide; 2,4-dimethoxy-5-bromo-N-(2-N-morpholinyl ethyl)benzenesulfonamide; 2,4-dimethoxy-5-bromo-N-(2-N-piperidinyl propyl)benzenesulfonamide; 2,4-N-dimethoxy-5-bromo-N-(2-N-morpholinyl-propyl)benzenesulfonamide.

10. The pharmaceutical composition of claim 9 wherein the compound is selected from the group consisting of 2,4-dimethoxy-5-chloro-N-(2-N-pyrrolidinyl ethyl)benzenesulfoanamide; 2,4 dimethoxy-5-chloro-N-(2-N-piperidinyl ethyl)benzenesulfonamide; 2,4-dimethoxy-5-chloro-N-(2-N-morpholinyl ethyl)benzenesulfonamide; 2,4-dimethoxy-5-bromo-N-(2-N-pyrrolidinyl ethyl)benzenesulfonamide and 2,4-dimethoxy-5-bromo-N-(2-N-piperidinyl ethyl)benzenesulfonamide.

* * * * *